(12) United States Patent
Centen et al.

(10) Patent No.: US 8,926,538 B2
(45) Date of Patent: Jan. 6, 2015

(54) SUPPORT DEVICE FOR ADMINISTRATION OF CPR

(75) Inventors: Corey Centen, Ottawa (CA); Sarah Smith, Hamilton (CA)

(73) Assignee: Physio-Control, Inc., Redmond, WA (US)

( * ) Notice: Subject to any disclaimer, the term of this patent is extended or adjusted under 35 U.S.C. 154(b) by 1219 days.

(21) Appl. No.: 12/171,755

(22) Filed: Jul. 11, 2008

(65) Prior Publication Data
US 2009/0171257 A1    Jul. 2, 2009

Related U.S. Application Data

(60) Provisional application No. 61/008,912, filed on Dec. 26, 2007.

(51) Int. Cl.
*A61F 5/00*     (2006.01)

(52) U.S. Cl.
USPC ............................................. 602/20; 602/21

(58) Field of Classification Search
USPC ................ 602/20–23; 128/878–879; 601/41
See application file for complete search history.

(56) References Cited

U.S. PATENT DOCUMENTS

| | | | | |
|---|---|---|---|---|
| 4,881,533 | A | * | 11/1989 | Teurlings ......................... 602/21 |
| 5,088,037 | A | | 2/1992 | Battaglia |
| 5,239,988 | A | | 8/1993 | Swanson et al. |
| 5,537,692 | A | | 7/1996 | Dorr |
| 5,600,849 | A | * | 2/1997 | Hu ..................................... 2/16 |
| 5,652,955 | A | * | 8/1997 | Skewis ............................... 2/20 |
| 5,759,166 | A | * | 6/1998 | Nelson et al. ................... 602/21 |
| 5,771,492 | A | | 6/1998 | Cozza |
| 5,928,172 | A | * | 7/1999 | Gaylord .......................... 602/21 |
| 5,987,641 | A | * | 11/1999 | Walker ................................. 2/16 |
| 6,526,592 | B1 | | 3/2003 | Best |
| 6,564,389 | B1 | | 5/2003 | Laughlin |
| 6,827,695 | B2 | * | 12/2004 | Palazzolo et al. ............... 601/41 |
| 6,834,397 | B1 | | 12/2004 | Murphy |
| 6,959,453 | B2 | | 11/2005 | Best |
| 7,122,014 | B2 | | 10/2006 | Palazzolo et al. |
| 7,245,964 | B2 | | 7/2007 | Moore et al. |

FOREIGN PATENT DOCUMENTS

| | | |
|---|---|---|
| WO | 01/79858 A1 | 10/2001 |
| WO | 2008/042765 A1 | 4/2008 |

OTHER PUBLICATIONS

Physio-Control, "Annotated Bibliography: Rescuer Fatigue with CPR", 2007, U.S.A.
A. Ashton, A. McCluskey, C.L. Gwinnutt, A.M. Keenan, "Effect of Rescuer Fatigue on Performance of Continuous External Chest Compressions Over 3 Min.", www.elsevier.com/locate/resuscitation.com, May 16, 2006, UK.
M.N. Spies-Dorgelo, D.A.W.M. Van Der Windt, H.E. Van Der Horst, A.P.A. Prins, W.A.B. Stalman, "Hand and Wrist Problems in General Practice—Patient Characteristics and Factors Related to Symptom Severity", Rheumatology 2007, Oct. 15, 2007.

* cited by examiner

*Primary Examiner* — Michael A. Brown
(74) *Attorney, Agent, or Firm* — Marger Johnson & McCollom, P.C.

(57) ABSTRACT

A support device for assisting a wearer in the administration of cardiopulmonary resuscitation (CPR), the device comprising: a wearable support for strengthening at least one of the wearer's wrist, hand or forearm, the wearable support being adapted to circumscribe a majority of the circumference of the at least one of the wearer's wrist, hand or forearm; wherein the wearable support is adapted to be in close contact with the at least one of the wearer's wrist, hand or forearm, to provide support to the wearer through compression of the at least one of the wearer's wrist, hand or forearm.

27 Claims, 11 Drawing Sheets

SUPPORT DEVICE FOR ADMINISTRATION OF CPR

TECHNICAL FIELD

This disclosure is related to the administration of cardiopulmonary resuscitation (CPR). In particular, this disclosure is related to support devices for administration of CPR.

BACKGROUND

For over forty years, the performance of effective chest compressions during CPR has been recognized as a key determinant in a victim's chance of survival from cardiac arrest. However, it is known that the proper administration of CPR is physically demanding, requiring the quick, consistent application of intense forces. Consequently, anatomical strain and physical fatigue are prevalent problems plaguing rescuers performing CPR. Recent changes in protocol have made CPR even more rigorous: a recommended compression to breaths ratio of 15:2 has been increased to 30:2.

A 2002 study concluded that rescuer fatigue adversely affects the quality of chest compressions when performed without interruption over a three minute period and that this effect may be more pronounced in females due to their smaller stature. Naturally, this conclusion may be extended to any healthy individual with smaller stature or lack of muscle tissue and bone structure in the wrist area. (Ashton et al., Effect of rescuer fatigue on performance of continuous external chest compressions over 3 min, Resuscitation 55(2002), 151-155). The study found that the rate of satisfactory compressions dropped from 82 to 52 over a three minute period. The study also indicated that optimally performed CPR provides only one third of normal cardiac output and so even a modest deterioration in performance may have a clinically significant adverse result.

Rescuer exhaustion is not the only factor preventing the effective performance of CPR; a significant portion of the population is unable to properly administer chest compressions due to wrist or hand diseases and disorders. Hand and wrist problems are common: a 2007 paper on hand and wrist ailments indicated that the incidence of new cases of wrist problems in the general population was 4.6/1000/yr and that of hand and finger ailments was 7.8/1000/yr (Hand and wrist problems in general practice—patient characteristics and factors related to symptom severity, Rheumatology 2007; 46:1723-1728). It was also indicated that 12.5% of the sampled population had some form of wrist or hand problem. Beyond injuries and generally weak bone structure, many common diseases can lead to a destabilizing of the wrist joint. For example, a 1999 study in the United States found that the prevalence of carpal tunnel syndrome is 50/1000 with an incidence of 1-3/1000/yr (Atroshi I, Gummesson C, Johnsson R, et al: Prevalence of carpal tunnel syndrome in a general population. JAMA Jul. 14, 1999; 282(2): 153-8). Carpal tunnel syndrome (CTS) is a collection of characteristic symptoms and signs that occurs following entrapment of the median nerve within the carpal tunnel. Usual symptoms include numbness and paresthesias and may be accompanied by objective changes in sensation and strength of median-innervated structures in the hand. Such a common disorder may preclude otherwise willing bystanders from being able to effectively perform CPR. Other wrist-related ailments such as arthritis and tendonitis are also common in the general population and especially among the growing population of the elderly who are most likely to be nearby when CPR is required.

Previously, certain cardiopulmonary resuscitation (CPR) assist and aid devices have been invented that instruct the user on the proper administration of CPR. One such device, disclosed in U.S. Pat. No. 5,239,988 to Swanson et al., is in the form of a wristwatch that includes audible signals that are emitted from a beeper at a rate dependent on which of a set of push buttons is pressed. This device is used in the timing of external heart massage or CPR. Although worn on the wrist, this device provides no support to the wrist, hand or arm and is simply designed to provide user instructions; feedback based on the quality of the rescuer's CPR is not provided by this device.

A second device, disclosed in U.S. Pat. No. 7,122,014 to Palazzolo et al., is a compression monitor that consists of accelerometers and tilt sensors to measure compression depth during the administration of CPR. In one embodiment, the accelerometer based device can be placed on the wrist or hand. Unlike the device disclosed in U.S. Pat. No. 5,239,988, this device provides feedback to the rescuer on parameters such as compression depth and rate. However, the device of Palazzalo et al. does not include any form of wrist, hand or arm support or guard to protect the affected joints and limbs of the rescuer during CPR.

Other rescue administration devices that may be worn on the wrist include those disclosed in U.S. Pat. Nos. 5,088,037 and 7,245,964. However, these devices are worn on the wrist only for convenience, and are not intended to provide any support or strengthening to the wrist.

Despite an abundance of CPR assist, monitoring and aid devices, there has yet to be a device designed to alleviate the symptoms and pains associated with joint discomfort and fatigue during the administration of CPR.

SUMMARY

The device presently disclosed addresses at least some of the challenges described above. In one aspect, the device may be worn on the wrist, hand, forearm or arm of the wearer. The device may be designed in such a way that it is easy to wear and use so that it does not delay the start of CPR in an emergency. The device may help in ensuring proper administration of CPR. The device may be used simply as a strengthening and support device or may additionally provide monitoring of CPR variables such as compression depth, compression rate, and compression angle. The device may be integrated into a wearable CPR assist device.

The device may additionally include sensors and/or feedback components that receive sensory input related to CPR parameters and provide feedback to the wearer based on this input. The present device provides physical support, structure and/or strength to the wearer's wrist, hand, forearm and/or arm. The present device may strengthen or stabilize the wearer's wrist, hand, forearm and/or arm through compression of the wrist, hand, forearm and/or arm.

In one aspect, there is provided a support device for assisting a wearer in the administration of cardiopulmonary resuscitation (CPR), the device comprising: a wearable support for strengthening at least one of the wearer's wrist, hand or forearm, the wearable support being adapted to circumscribe a majority of the circumference of the at least one of the wearer's wrist, hand or forearm; wherein the wearable support is adapted to be in close contact with the at least one of the wearer's wrist, hand or forearm, to provide support to the wearer through compression of the at least one of the wearer's wrist, hand or forearm.

In some embodiments, the support device may include a support plate on the wearable support, which is substantially rigid and adapted to be in close contact with the wearer's forearm, wrist and/or hand.

The support device may include sensors and/or feedback components to further assist the wearer in performing CPR.

The support device may be incorporated into a wearable CPR assist device that senses CPR parameters and provides feedback to the wearer.

BRIEF DESCRIPTION OF THE DRAWINGS

Aspects of the present disclosure will be discussed in detail below, with reference to the drawings in which.

DETAILED DESCRIPTION

The device as presently disclosed may provide support and strength to the wrist, hand, forearm and/or arm of both healthy and afflicted individuals during the administration of CPR. Furthermore, the device may alleviate symptoms associated with wrist, hand, forearm and/or arm ailments during the performance of CPR.

The support device may maintain the CPR administrator's hand and/or wrist at the proper angle relative to the forearm or arm to promote maximal force transfer during CPR, thereby reducing fatigue. Furthermore, the device may alleviate symptoms of wrist disease or pain, such as arthritis and carpal tunnel syndrome, by strengthening the joint and reducing unnecessary strains and stresses. The device may strengthen the arm, forearm, hand and/or wrist, providing the wearer with added comfort and endurance during the strenuous and demanding CPR process. Those with smaller stature and/or weak joints may especially benefit from the device. This device may provide physical support to the wearer during the administration of manual CPR, which is not provided by the prior art CPR assist, monitoring or instructing devices described above.

Generally, the support device comprises a wearable support. The wearable support may be snug and worn in close contact against the wearer's wrist, hand, forearm and/or arm in order to provide support to the wearer's wrist, hand, forearm and/or arm through compression of the wrist, hand, forearm and/or arm. The support device may have a fastener for fastening the wearable support in close contact with the wearer's wrist, hand, forearm and/or arm. The support device may have a support plate also in close contact against the wearer's wrist, hand, forearm and/or arm, which may be relatively rigid, to provide further support. The support plate may be removably held in place by the wearable support, for example by inserting the support plate into a pocket on the wearable support. In some embodiments, the support device may include features that improve the administration of CPR, as described below. The wearable support may be adjustable (e.g., elastic or with an adjustable fastener) in order to be snug for wearers of different sizes. In some embodiments, the wearable support may be a wrist strap, palm strap, glove, or arm band. In this description, the CPR administrator or rescuer is also referred to as the wearer.

Figure 1:
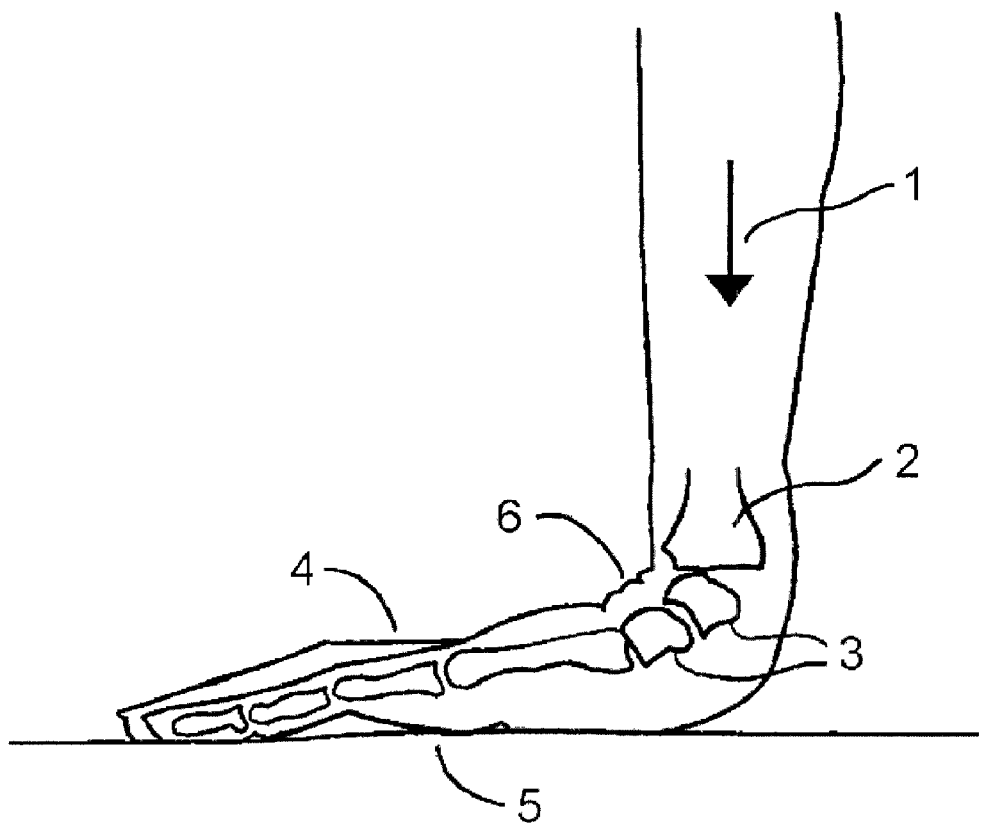
FIG. 1 is an illustration showing a hand and wrist joint experiencing axial loading forces during the administration of CPR.
Figure 2:
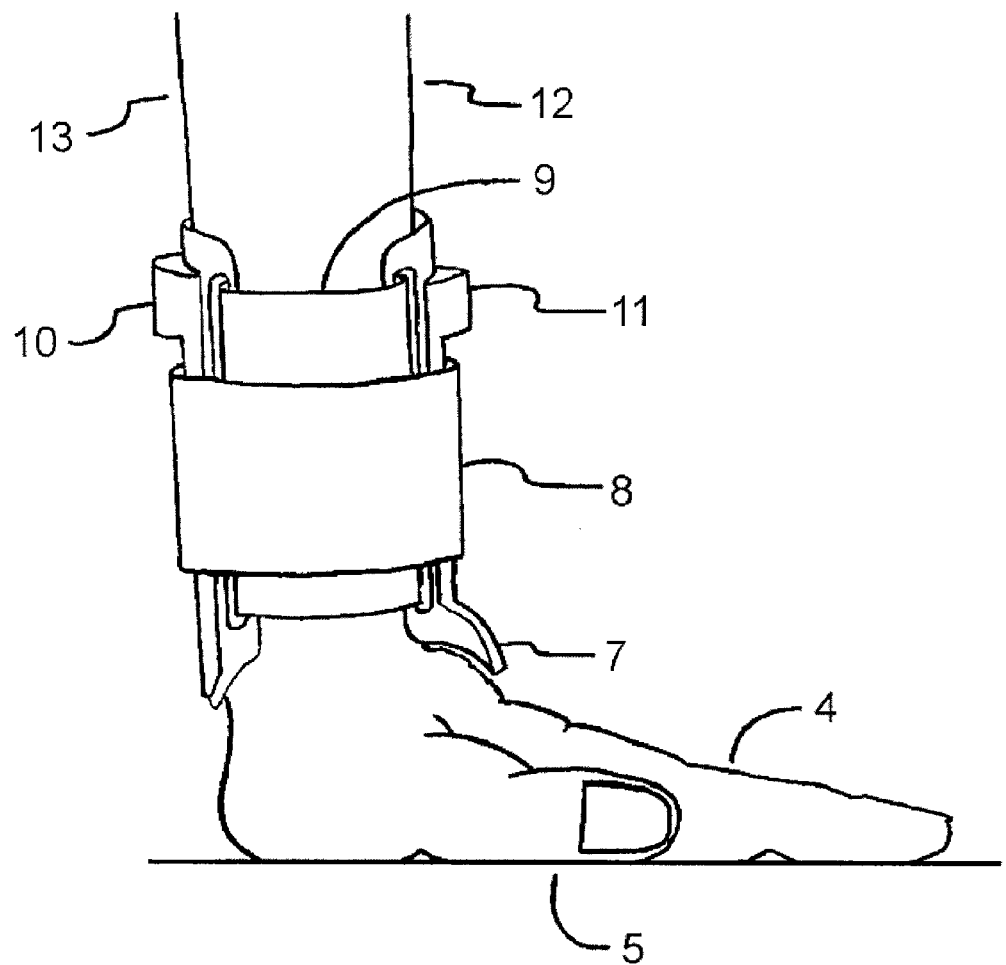
FIG. 2 is a side plan view of a support device with support plates in accordance with an embodiment.
Figure 3:
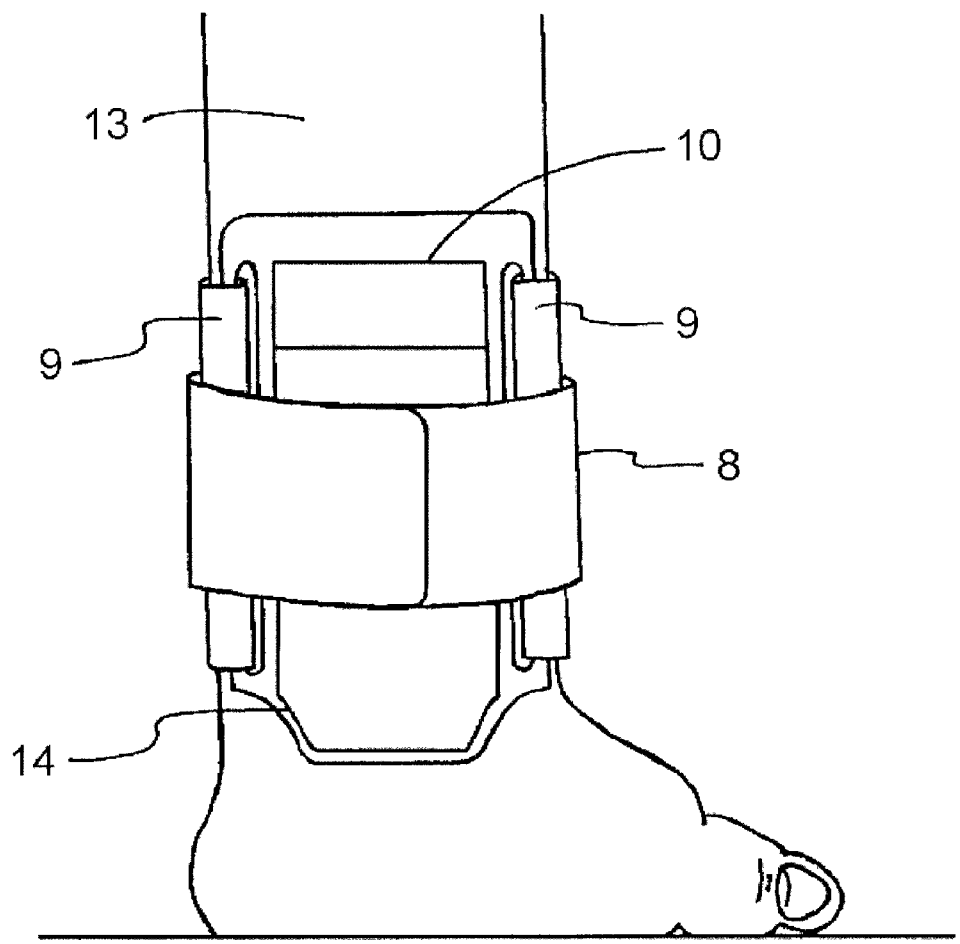
FIG. 3 is a rear plan view of the support device of FIG. 2.

Reference is now made to FIG. 1, which shows the forces present in the hand, wrist and arm of a CPR administrator or rescuer. During the administration of CPR, significant axial forces 1 are present on the rescuer's wrist joint 6, as shown. Other portions of the rescuer's arm, such as the forearm, also experience high forces during CPR administration. These forces are generated by the downward thrust of the rescuer's torso and arms and borne by the wrist 6, and dorsal 4 and plantar 5 sides of the hand. For effective CPR, the forces should be capable of compressing the victim's chest at a suitable rate to a suitable depth, for example 4-5 cm at a rate of 100 compressions per minute, and may pose a serious risk of injury and discomfort to the rescuer. The cyclical stresses exerted on the rescuer's limbs and joints during CPR not only pose a risk of injury, but may also lead to rescuer fatigue and an inability to continue the CPR until further help arrives.

The support device may be used to strengthen a person's wrist joint, hand, forearm and/or arm during the administration of CPR, through compressive support of the wrist, hand, forearm and/or arm. By compressing the wrist, hand, forearm and/or arm, the support device may support the soft tissues in the area of interest. Such compressive support may also allow enhancement of the elasticity of tendons and ligaments through the controlled maintenance of body heat in the area of interest.

The device may be used in the administration of CPR in an emergency or in the practicing of CPR for training purposes. The device may assist a healthy individual to administer CPR for a longer duration of time without experiencing the ill-effects of fatigue and joint soreness. Furthermore, the device may help prevent injury or pain to a healthy individual while administering CPR for an extended period of time. A number of potential injuries are possible including dorsal wrist impingement wherein the dorsal edge of the radius 2 impinges on the wrist bones 3. Paramedics, doctors, nurses and other medical professionals or first aid responders who perform CPR regularly and for lengthy time intervals may find such a device particularly useful.

Furthermore, the support device may be used by persons suffering from hand, wrist, forearm and/or arm problems. The device may provide strength and/or stability to an otherwise weak joint. The device may enable those suffering from ailments such as, but not limited to, carpal tunnel syndrome, arthritis, tendonitis, and osteoporosis to effectively provide CPR. Furthermore, the device may enable those with wrist, hand, forearm and/or arm injuries such as sprains or joint soreness to perform CPR more efficiently. The device may assist in protecting the wrist joint, hand and/or the forearm and its associated muscles, tendons, bones and nerves.

FIGS. 2-4A illustrate an embodiment of the support device, in this case providing support to the wrist. Here, the support device includes two support plates. In this example, the support plates are designed to conform to and support the wrist, and are also referred to as wrist modules. The device has a ventral wrist module 10 designed to be in close contact with the ventral forearm 13 of the wearer and a dorsal wrist module 11 designed to be in close contact with the dorsal forearm 12 of the wearer. The two wrist modules 10, 11 are held in place by a wearable support, such as an elastic strap 9. The wrist modules 10, 11 may be relatively rigid plates that are held in compression against the wearer's arm by the elastic strap 9. Further compression may be provided by a wrap-around compression strap 8. The compression strap 8 may be tightened by the wearer and held in place with a fastener such as an adhesive material, a buckle, a hook and loop fastener, or other fastening means. This embodiment of the support device also includes a hyperextension barrier 7 integral with the dorsal wrist module 11. The hyperextension barrier 7 comprises a relatively rigid portion of material, and has a protrusion at a fixed angle for preventing over-extension of the wrist joint during administration of CPR. The ventral wrist module 10 is inserted into a ventral wrist pocket 14 and the dorsal wrist module 11 is inserted into a dorsal wrist pocket 15. The pockets 14, 15 are provided on the elastic strap 9, and allow the modules 10, 11 to be interchanged and replaced easily. The modules 10, 11 may be removed and the remaining components may be cleaned or sterilized separately.

In this example, the support plates are wrist modules 10, 11 that provide support to the wearer's wrist, however other support plates may be designed to provide support to other portions of the wearer's wrist, hand, forearm and/or arm. Although two support plates are shown, there may be one, two, three or more support plates, which together may circumscribe only a portion, a majority, or all of the circumference of the wrist, hand, forearm and/or arm. Variations may include support plates that extend further up one or both sides of the arm to provide further support to the wearer's forearm. The support plates may be slightly curved to conform to the wearer's wrist, hand and/or forearm, as shown, or may be substantially planar. The support plates may be made of any material that offers suitable stiffness. For example, the support plates may be made of a hard polymer material such as polypropylene or polyethylene. The chosen material may be relatively light to reduce the weight of the device and to reduce encumbering the wearer. The material may be chosen to be easily cleaned or sterilized. If there is more than one support plate, the material of each may be different, for example in cases where extra stiffness is desired for the ventral side but not for the dorsal side. Although described as a plate, the support plate may include a panel, a shell, or other similar support structures.

In this example, the support plates and the wearable support are held in close contact with the wearer using an adhesive band as the fastener. However, any fasteners that may be used to tightly hold the wearable support and/or support plates against the wearer may be suitable. For example, the wearable support may be held using lacing, a belt, a continuous elastic band, and other similar fasteners. Alternatively, the wearable support may hold itself in place, for example because it is an elastic sleeve, such that no additional fasteners are required to hold the wearable support and/or support plates in place. Where a support plate is provided on the wearable article, the support plate may be removable from the wearable article for ease of cleaning or disposal. For example, the support plate may have openings which the wearable article may loop or hook through, or the support plate may be removably attached to the wearable article, for example using hook and loop fasteners, snap buttons, or weak adhesives. The wearable support or the fastener may be adjustable (e.g., elastic) or exchangeable to allow the support device to be tightly worn by wearers having different wrist, hand or arm sizes.

The hyperextension barrier 7 prevents hyperextension of the wearer's hand during compression, and may improve the administration of CPR by ensuring that the wearer's hand is kept at a recommended angle to the wearer's forearm. As shown, the hyperextension barrier 7 has a body conforming to the dorsal side of the wearer's arm, and has a protrusion or lip at a fixed angle from the body of the hyperextension barrier 7, which is intended to protrude over the back of the wearer's hand, thus preventing the hand from flexing back beyond the fixed angle. The hyperextension barrier 7 may be a separate component, which may be removable from the device, for example in a manner similar to the wrist modules 10, 11, or may be integral with the wearable article or the support plate, for example the dorsal wrist module 11. In some embodiments, the device does not have a hyperextension barrier 7. The hyperextension barrier 7 may prevent the movement of the wrist beyond its natural position during the administration of CPR. The hyperextension barrier 7 may be different from that used in gymnastics or sports in that it is designed to sustain and encourage a desired hand-to-forearm angle for a lengthy period of time (e.g., the time required for complete administration of CPR) as opposed to short, instantaneous incidences, as in sports. The hyperextension barrier 7 may be made of a rigid, yet pliable material, and may conform to the back of the wearer's hand. Providing a shape conforming to the wearer's forearm and/or wrist (e.g., a curved shape) may provide added comfort and/or support to the wearer while preventing movement of the wrist beyond its natural position. The hyperextension barrier 7 may additionally include padding or cushioning on the side in contact with the back of the wearer's hand, to provide added comfort and/or support.

Figure 4A:
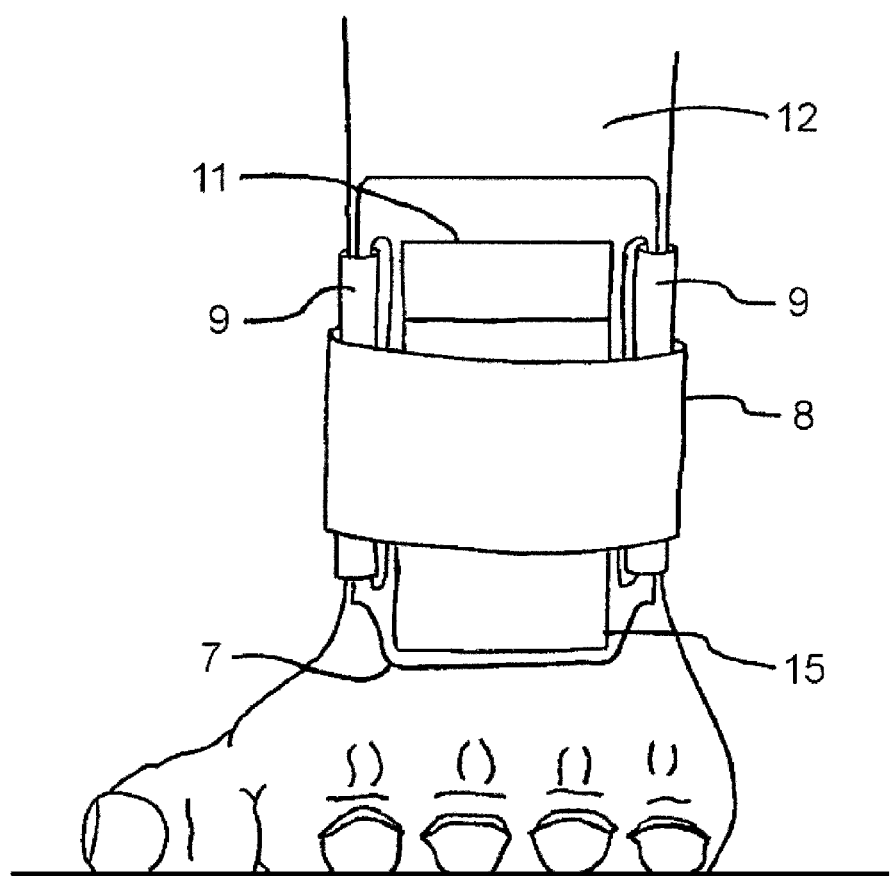
FIG. 4A is a front plan view of the support device of FIG. 2.
Figure 4B:
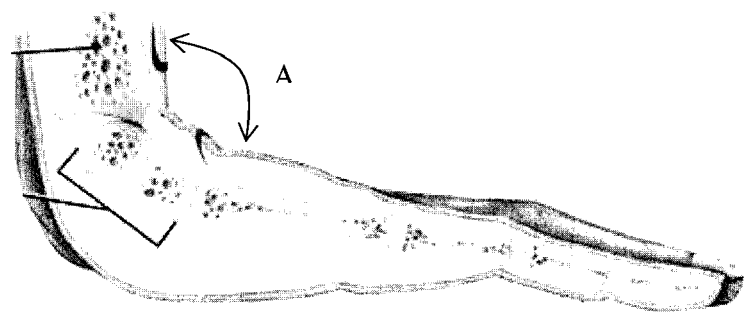
FIG. 4B is an illustration showing a bent wrist joint.

The hyperextension barrier 7 may also assist the wearer to perform CPR at a proper or desired position, for example with the hand at 90 degrees to the wrist and/or arm, without overextending the wrist joint. Hyperextension typically occurs when the angle between the back of the hand and forearm exceeds about 90 degrees. Thus, the hyperextension barrier 7 may protrude from the device at a fixed angle of about 90 degrees to encourage this proper or desired position. This fixed angle typically would not be a strict angle, for example a strict 90 degrees, as the wrist joint between the hand and forearm is not an abrupt angle. Rather, the hyperextension barrier 7 may be curved to conform to the curved shape of the wrist joint. With reference to FIG. 4B, a bent wrist typically curves into an angle A, which may be about 90 degrees. Thus the hyperextension barrier 7 may be designed to match this natural curved shape.

Figure 5:
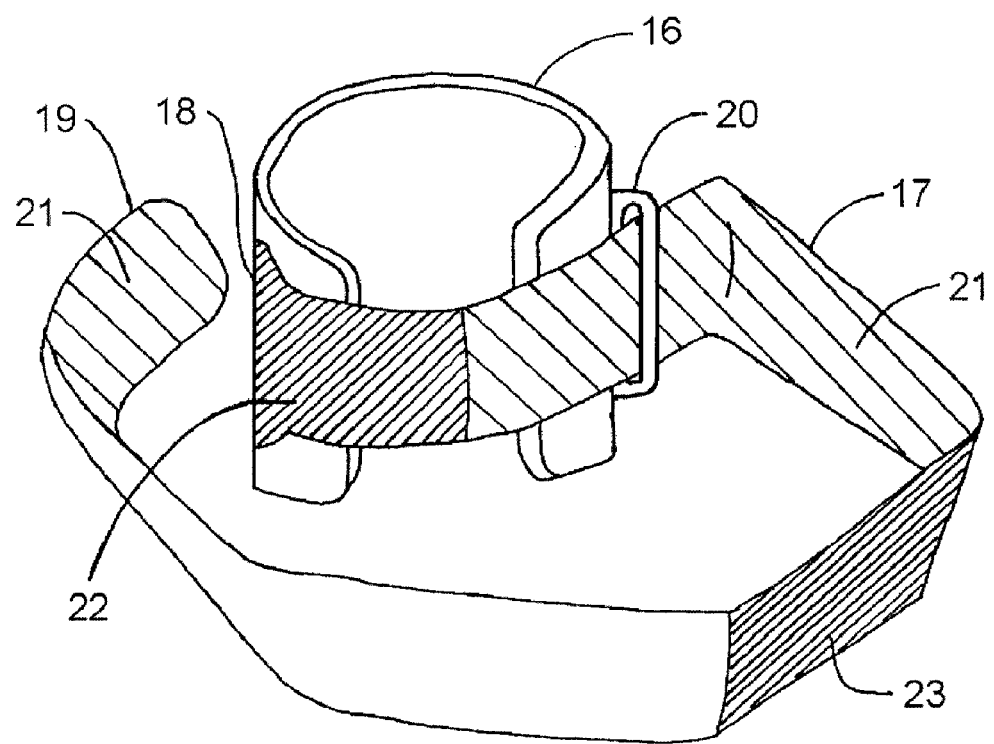
FIG. 5 is an illustration showing a support device with a wrist band in accordance with another embodiment, in its open position.
Figure 6:
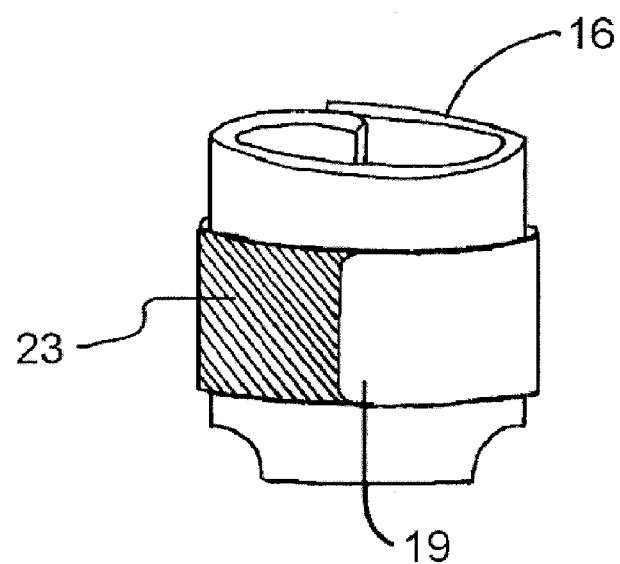
FIG. 6 is an illustration showing the support device of FIG. 5 in its closed position.
Figure 7:
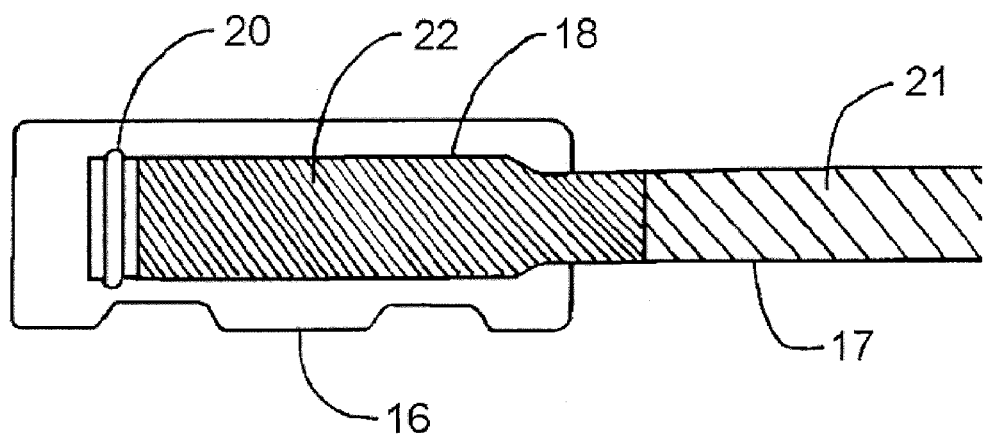
FIG. 7 is a side plan view of the support device of FIG. 5 in its open position.

FIGS. 5-7 show another embodiment of the support device, which provides support to the wrist. In this embodiment, the wearable support is in the form of a compression wrist band 16. The support device of FIG. 5 is designed to provide support to the wearer's wrist, and includes a wearable support such as a wrist band 16 which is of a length sufficient to circumscribe most or all of the greater circumferential extent of the wearer's wrist, and also includes a fastener. The fastener may be in the form of a flexible strap 17 superimposed on the band 16. The flexible strap 17 may have one end portion 18 which is attached to the band 16 and a free end 19 opposite to the attached end. The strap 17 extends in a direction parallel to the length of the band 16 and is of a total length to encircle the band 16 and wrist at least once when applied to the wrist of the wearer. The wrist band 16 includes a buckle or fastening loop 20 so that the free end 19 of the strap can be passed through the loop 20, then returned or reversed in direction upon itself, as illustrated in FIG. 6. For clarity, FIG. 7 shows the device in an opened configuration. Briefly, once the strap 17 is tightened around the wrist to the desired degree, an engagement device or adhesive material 21 on the loose end may be brought into contact with a second engagement device or adhesive material 22 in order to securely but releasably fasten the loose end to the desired degree of tautness. The flexible strap 17 further may have a third engagement device or adhesive material 23 that enables the remaining portion of the flexible strap 17 to circumscribe the wrist completely and adhere unto itself. Other variations for fastening the flexible strap 17 are possible, including hook and loop fasteners, snap fasteners, and buckles.

The wrist band 16 is shown as forming a complete circumference, however the wrist band 16 need not form a complete circumference around the wearer's wrist and may only circumscribe a majority of the circumference of the wearer's wrist. The device may still provide sufficient support without completely circumscribing the wearer's wrist as long as the wrist band 16 covers a majority of each of the ventral and the dorsal sides of the wrist. Alternatively, the wrist band 16 may overlap itself at the ends when forming a circumference, as shown in FIG. 6, as long as this overlap does not interfere with securing the device to the wearer's wrist.

For this example, the device may be designed to be worn by wearers of different sizes and builds by ensuring that the wearable support, in this case the wrist band 16, is sufficiently long to circumscribe at least a majority of the circumference of the wearer's wrist where the wearer is of large build (e.g., in the top ten percentile of wrist size) while preventing excessive overlap when worn by a wearer having a smaller build (e.g., in the bottom ten percentile of wrist size). Alternatively, the device may be provided in different size or size ranges to accommodate wearers of different builds and sizes. The wrist band 16 may also be provided in different widths, for example to extend the device from the wrist up the forearm of the wearer, to offer different amounts of support. The width may also be different corresponding to different portions of the wearer's wrist, hand and/or forearm. The wrist band 16 may be elastic or pliable, such that a single size may be stretched as necessary to accommodate wearers of different builds and sizes while still providing support through compression of the wrist and/or forearm.

The wearable support may be made of a material that is flexible enough to be opened up and wrapped around a wrist, while providing support through compression. For example, the wearable support may be made of a tightly-wound material, such as neoprene. The material for the wearable support may be chosen to be easily cleaned and sterilized. Alternatively, the wearable support or a portion of the wearable support may be rigid or semi-rigid, to provide additional support.

In this example, the wrist band 16 may also include a hyperextension barrier on a portion that is intended to be worn on the ventral side of the wearer's wrist, similar to that described above. The hyperextension barrier may be integral to the wrist band 16 or may be removable from the wrist band 16, similar to that described for the support plate. The wrist band 16 may also have portions of different rigidity in order to provide support at the appropriate location on the wrist, for example a portion intended to be worn on the ventral side of the wearer's wrist may be made more rigid than a portion intended to be worn on the dorsal side.

The strap 17 is shown as folding back upon itself, however the strap 17 may also simply wrap around itself, with or without the presence of a loop 20. The strap 17 may adhere to itself using adhesive material on its surface, as described above. The strap 17 may alternatively or in addition fasten to itself by the use of other fasteners, such as buckles, snap buttons, or hook and loop fasteners. The strap 17 may alternatively or in addition fasten to the wrist band 16 by the use of fasteners on the wrist band 16, for example in cases where the strap 17 is not long enough to wrap around itself. The strap 17 may be made of a flexible material, and may be elastic, to aid in tightening the device around the wearer's wrist. Although the strap 17 is described as having an end portion 18 attached to the wrist band 16, the end portion 18 may be removably attached, so that the wrist band 16 and the strap 17 can be separately disposed of or cleaned for reuse. Although the device is shown with a strap 17 for fastening the device to the wearer, other fasteners may be suitable, such as lacing or buckles, or a fastener may not be necessary, for example where the wrist band 16 is instead an elastic sleeve.

Figure 8:
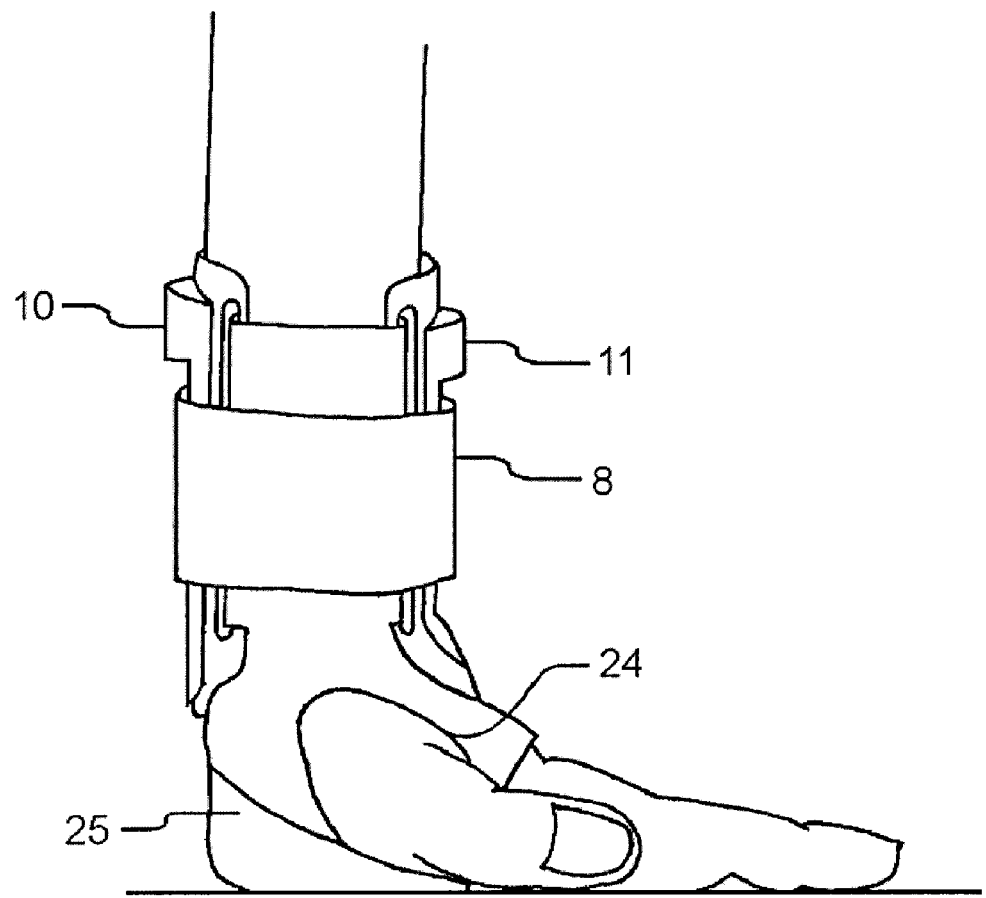
FIG. 8 is a side plan view of a support device with thumb loop and palmar pad in accordance with another embodiment.

FIG. 8 shows another embodiment of the device in which the wearable support is in the form of a wrist support that extends to the lower part of the wearer's hand. The design of the wearable support surrounding the ventral and dorsal wrist and/or forearm may be similar to the previously described embodiments. Although this embodiment is illustrated as a modification of the embodiment described with reference to FIGS. 2-4 above, similar modifications may be made to the embodiment described with reference to FIGS. 5-7 above. The wearable support may be provided with a thumb loop 24 to anchor the support in place and to help orient the device on the wearer's hand.

The device may include a palmar pad 25 designed to correspond to the palm or plantar side of the hand inside the lower portion of the support. The palmar pad 25 may extend from the wrist joint towards the mid region of the wearer's palm where the palmar pad 25 terminates. The palmar pad 25 may provide further support by elevating the wrist joint to a more comfortable elevation angle relative to the hand. For example, the palmar pad 25 may have a fixed elevation angle corresponding to the heel of the wearer's palm, for example an angle of about 45 degrees, and may be curved to conform to the shape of the palm and bent wrist. When the palm and wrist is at an elevated angle, there is typically less stress and strain on the joint and its associated tendons, muscles and bones. An elevation may also reduce the risk of dorsal wrist impingement. The palmar pad 25 may promote a more natural position for the administration of compressions during CPR, thus reducing fatigue and increasing wearer comfort. Additionally, the palmar pad 25 may also cushion the wrist joint, carpal bones and/or nerves from high impact loads such as those experienced during the administration of CPR. The palmar pad 25 may be relatively rigid to provide support at an elevated angle. For example, the palmar pad 25 may be made of a rigid polymer material, similar to the material for the support plate and/or the hyperextension barrier. The palmar pad 25 may be removable for ease of cleaning or disposal, and so that the device may fit wearers having different hand sizes.

Although the thumb loop 24 and the palmar pad 25 are both shown in FIG. 8, the device may include only the thumb loop 24 or only the palmar pad 25. The thumb loop 24 and the palmar pad 25 may be integral to each other, or they may be separate. The thumb loop 24 and/or the palmar pad 25 may be easily removable from the device for ease of disposal or cleaning. In addition to the thumb loop 24, one or more loops may be provided for the other fingers. Instead of a simple thumb loop 24 and/or finger loops, the device may be provided in the form of a glove. When worn, the glove may provide compressive support to the proper areas of the wearer's wrist, hand, forearm and/or arm. Where there is a support plate, the glove may position the support plate to provide suitable support to the wearer's wrist, hand, forearm and/or arm. The glove may be fitted to the wearer so that the support plate is held sufficiently tightly against the wearer to offer support. Alternatively or in addition, fasteners or tightening devices (e.g., lacing or buckles) may be provided on the glove to further tighten device against the wearer.

The thumb loop 24 may be made of a soft and/or elastic material so as to adapt to differently sized hands. The thumb loop 24 may be designed to be openable, so that it may wrap around the wearer's thumb and fastened closed once secured around the thumb.

A feature of the support device is its ability to promote proper CPR technique. In certain embodiments, the device encourages the wearer to maintain his or her forearm perpendicular to his or her hand. In one embodiment, the hyperextension barrier is designed to rest against the back of the hand for promoting a desired or proper CPR position. When the hyperextension barrier rests against the back of the hand, the wearer is aware that he or she is performing the CPR at the desired or proper angle and is thus transferring the maximum amount of force with the least amount of effort. Consequently, this desired or proper technique may lead to a reduction in fatigue and an increase in the maximum transferable force to the chest of the victim. In another embodiment, the portion of the support device adjacent the dorsal forearm may extend below the wrist joint encouraging the wearer to maintain his or her hand perpendicular to the forearm.

Figure 9:
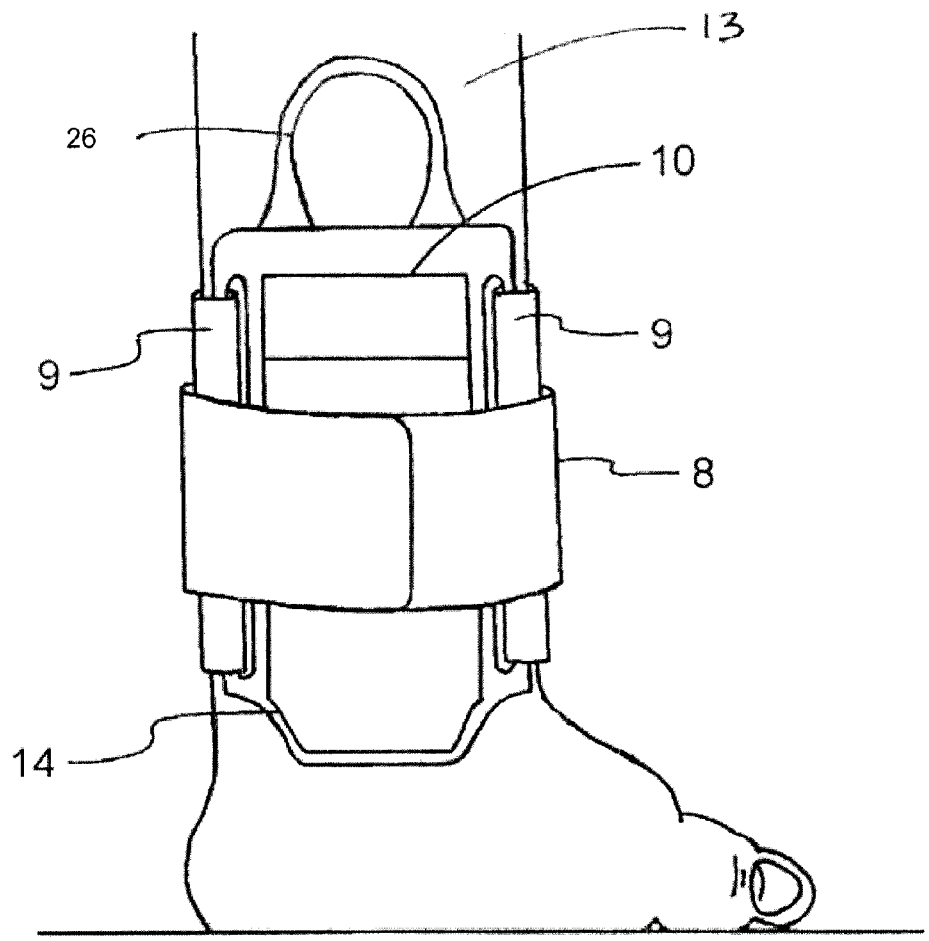
FIG. 9 is an illustration showing a support device with an appendage in accordance with another embodiment, in its closed position.
Figure 10:
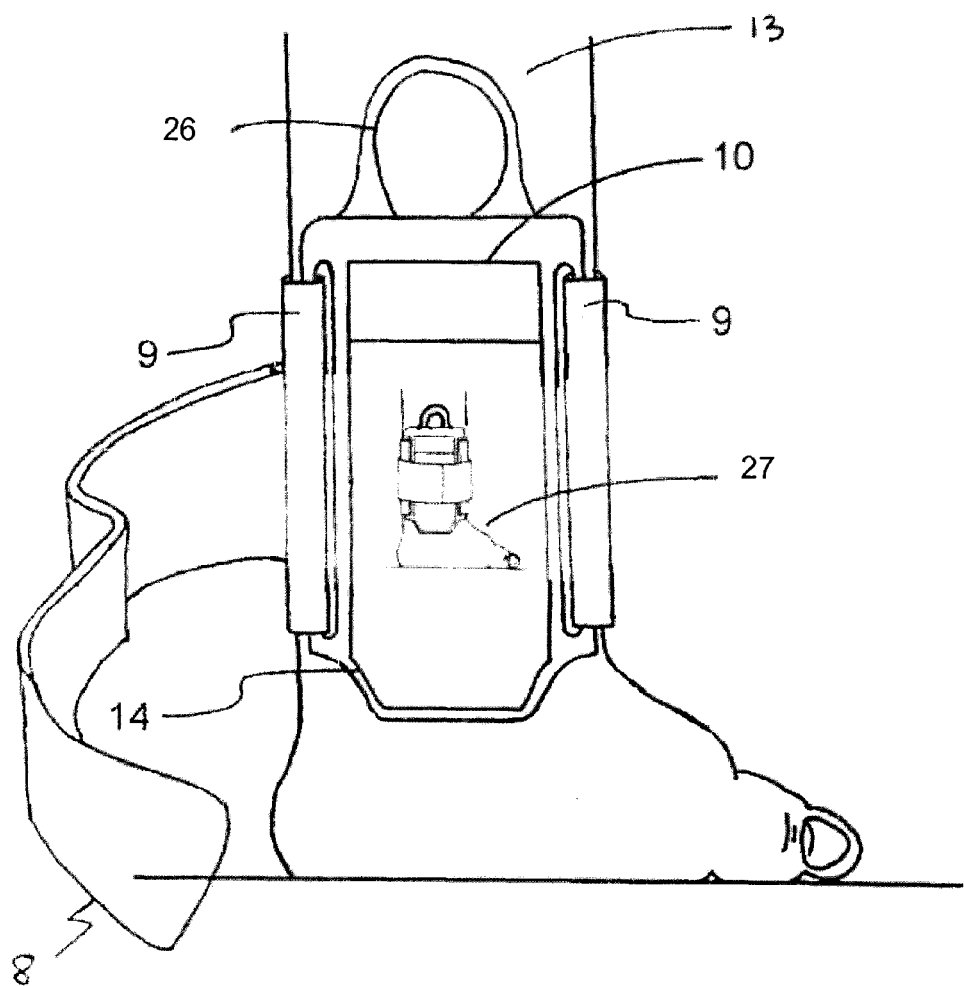
FIG. 10 is an illustration showing the support device of FIG. 9 in its open position.

Reference is now made to FIGS. 9 and 10. In some embodiments, the support device may be designed to be easily slipped on by the wearer, with minimal effort. This may be useful in emergency situations where CPR should be delivered with minimal delay. To facilitate wearing of the device, an appendage such as a hook or a loop 26 may be included on the wearable support, which may be grasped with one hand in order to pull the device over the opposite hand. The device may have a simple cylindrical design that makes it intuitive to wear and/or use. Although some embodiment may include thumb loops and/or finger holes, other embodiments may be designed to be worn on the right or left hand, for example being in the shape of a simple cylinder. There may additionally be images, instructions, arrows, or other indications 27 on the device to indicate the proper wearing and/or use of the device. As well, the device may be designed to avoid impeding motion of the hand, wrist and/or arm, by using flexible materials where natural motion is desired. However, a relatively rigid hyperextension barrier may still be included to prevent the unnatural hyperextension of the wrist.

Although the support device may be adjustable to fit different wearers by providing a fastener that is adjustable (e.g., lacing or a buckle), the fastener or wearable support itself may alternatively or additionally be elastic in order to accommodate different wearers. The wearable support itself may be made of an expandable, flexible, and/or elastic material that allows the device to expand and contract to fit various hand and/or arm sizes. The device may be stretched easily when placing it on, for example, the wearer's wrist, but may easily contract once in position, thus compressing to the wrist area to provide support.

Although shown as being worn around the wrist, the support device may also be worn around the forearm, to provide support to the forearm. Such a forearm support may be worn above the wrist, to provide compressive support to the forearm during administration of CPR. Such a forearm support device may cover only a portion of the forearm and not the wrist joint itself. A hyperextension barrier may be provided on the support device. The hyperextension barrier may descend from the support device around the forearm, and include a protrusion over the back of the hand, for preventing overextension of the wrist as described above.

The materials chosen for the different components of the support device may depend on the intended use. Where the support device is designed to be for one-time-use and disposable, the materials may be inexpensive materials. For example, the elastic strap 9, compression strap 8, the wrist strap 16 and the flexible strap 17 may be made of a light fabric composite or inexpensive plastic, and the support plate, hyperextension barrier and/or palmar pad may be constructed of an inexpensive relatively rigid material, such as a rigid cardboard. For a multi-use or sterilizable device, the chosen materials may be higher quality. For example, the elastic strap 9, compression strap 8, wrist strap 16 and the flexible strap 17 may be made of a durable fabric such as neoprene, spandex or leather, while the support plate, hyperextension barrier and/or palmar pad may be constructed of a durable relatively rigid polymer, such as polypropylene or polyethylene. If used in an environment subject to water, the support device may comprise waterproof materials or coatings.

In some embodiments, the support device may include a feedback component and/or a sensor, which may aid the wearer in proper administration of CPR. Such components or sensors may be provided as embedded electronics in the support plate. For example, the dorsal wrist module and ventral wrist module described above may contain embedded electronics. Alternatively or in addition, feedback components and/or sensors may be provided on the wearable support. The wearable support and/or support plate may contain pockets or extra fastening mechanisms allowing the feedback components and/or sensors to be removably attached. The feedback component may be useful in providing guidance to the wearer on how to perform the CPR. The feedback component may provide audio feedback, for example a metronome to help pace the wearer in performing the compressions at the proper rate. The feedback component may be a visual cue such as a light flashing at a certain rhythm, to help establish a proper or desired compression rate.

The sensors may sense certain parameters relevant to CPR administration, such as compression rate, compression depth, and compression angle. The information from the sensors may be provided to the wearer through the feedback component, to aid the wearer in proper administration of CPR. The information of the sensors may also be analysed to determine whether CPR is being properly administered, and the feedback to the wearer may be based on this analysis. Thus, the sensors and the feedback component may ensure that the wearer administers CPR according to a suitable protocol. An example of the feedback components and sensors that may be implemented in this device is described in U.S. patent application Ser. No. 11/936,184, the disclosure of which is hereby incorporated by reference in its entirety. For example, the sensors may be physiological sensors, pressure sensors, position sensors, or movement sensors. Suitable physiological sensors include electrocardiogram sensors, oximetry sensors, body type sensors, and body temperature sensors. Suitable pressure sensors include piezoelectric sensors, mechanical sensors, strain sensors, and capacitive sensors. Suitable position sensors include accelerometers, angle sensors, tilt sensors, optical sensors, and ultrasonic position sensors. Suitable movement sensors include accelerometers, angle sensors, and tilt sensors.

For example, a compression angle monitor, for example in the form of an accelerometer, tilt sensor, orientation sensor or mechanical sensor, may be incorporated into the support device, with suitable feedback (e.g., audio beeps or vibrations) to further warn the wearer that his or her compression angle must be adjusted for optimal CPR.

In particular, suitable feedback components may provide visual feedback, audio feedback, or tactile feedback. For example, this may be provided in the form of a display, an audio output device, or a tactile output device. Suitable displays include liquid crystal displays. Suitable audio output devices include tone generators, buzzers, and piezo elements. The feedback information may include audio cues, such as a voice prompt, indicating a proper or desired CPR protocol.

The feedback component or sensor may be integral to the device, for example being embedded in the support plate, or may be removably attached. Removal of the feedback component or sensor may be desirable to enable interchange of the feedback component as needed, or to enable disposal or cleaning of the device without damaging the feedback component or sensor.

The feedback information from the feedback component may provide feedback based on parameters sensed by the sensor (e.g., instructions to compress faster or slower), or may provide feedback or guidance unrelated to sensed parameters (e.g., audio instructions to tilt the patient's head before beginning breaths). The feedback information provided to the wearer may be the sensed parameters in the raw form, or may be the result of analysis of the sensed parameters. The feedback information may aid the wearer to conform to a proper or desired CPR procedure, for example by comparing the value of the sensed parameter to the desired value and providing feedback accordingly. The feedback component may provide indication that the wearer is within and/or outside of a proper or desired range of CPR parameters (e.g., compressing angle, compression rate and/or compression depth).

Figure 11:
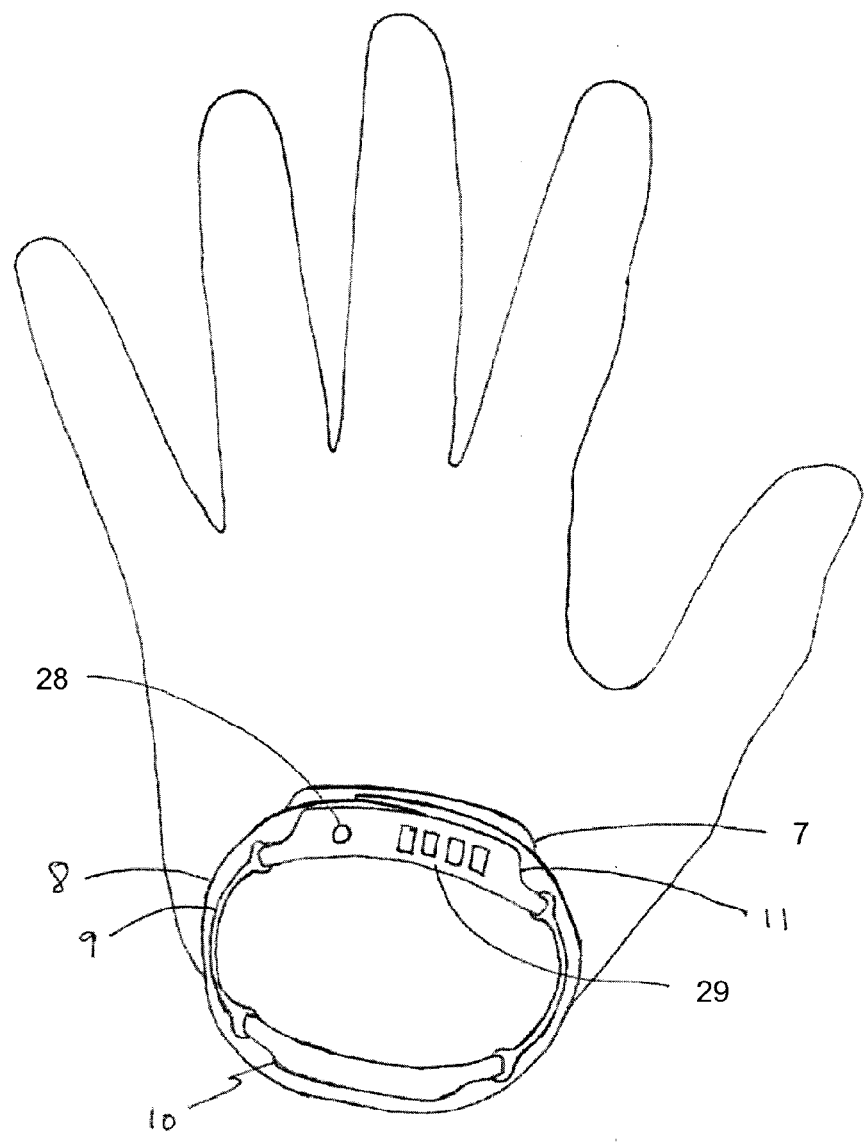
FIG. 11 is an illustration showing a support device having a feedback component in accordance with another embodiment.

Reference is now made to FIG. 11, which shows an embodiment of the support device that provides simple visual feedback to the wearer. The embodiment shown provides support to the wrist of the wearer, and includes a hyperextension barrier 7. This example includes a compression depth sensor (e.g., an optical sensor, an electromagnetic coil, or an accelerometer). Here, the feedback component may include a compression rate indicator 28, which may be a LED that lights in a proper or desired rhythm, to guide the wearer to provide CPR compressions at a certain rate. The feedback component may also include a compression depth indicator 29, which may be a bar of LED lights that light up in response to the sensed compression depth. For example, if the compression is too shallow, the compression depth indicator 29 may only light up partway, to indicate to the wearer that the compression depth is insufficient. Alternatively or in addition, the compression depth indicator 29 may light up in a red colour, to indicate that the compression depth is incorrect. The feedback component in this example is integral to the dorsal wrist module 11.

Although not described in detail here, the support device may be incorporated into a CPR assist device as described in the above-referenced U.S. patent application Ser. No. 11/936,184, which includes a sensor, a feedback component, and a processing unit. The processing unit may be configured to receive a sensed parameter from the sensor and send information based on the sensed parameter to the feedback component, to be conveyed to the wearer. The device may be incorporated into a wearable CPR assist device such as a CPR assist glove, with or without fingers, and may be used in conjunction with a base station, a monitoring station, or a computing station as described in the above-mentioned patent application. The support device may also aid in CPR training. In particular, where the support device has a hyperextension barrier, the device may aid in teaching a proper angle for CPR administration.

The support device may be designed so as to not limit the range of motion of the wearer. For example, a wrist support device may provide strength and stability to the wearer's wrist while allowing rotation, flexion and extension of the wrist. For individuals performing CPR routinely, such as paramedics and first responders, the device may be wearable at all times and not limit any other required activities. Furthermore, the device may be easily folded and stored, for example in an emergency kit or alongside a defibrillator so as to be accessible in emergency situations.

The support device is in no way limited to the specific embodiments described. All examples are for the purpose of illustration only and are not intended to be limiting. Any device for strengthening or stabilizing the wrist during CPR, improving comfort during CPR, alleviating symptoms of disease or injury during CPR, decreasing fatigue through physical support during CPR or helping to properly orient the hands and wrist during CPR may be covered by this application. Furthermore, the support device described herein may provide support, strength or protection to other joints of the wearer during CPR such as the elbow and shoulder. The scope of this application is not to be limited by the listing of specific components. Any materials, textiles, plastics or electrical or computing components may be used to satisfy the goal of the invention, as would be understood by a person skilled in the art. All references mentioned are hereby incorporated by reference in their entirety.

The invention claimed is:

1. A support device for assisting a wearer in the administration of cardiopulmonary resuscitation (CPR), the device comprising:
    a wearable support for strengthening at least one of the wearer's wrist, hand or forearm, the wearable support being adapted to circumscribe a majority of the circumference of the at least one of the wearer's wrist, hand or forearm; and
    a substantially rigid hyperextension barrier provided on the wearable support, the hyperextension barrier having a body and a protrusion extending at a fixed angle of about 90 degrees from the body of the hyperextension barrier, the body of the hyperextension barrier being adapted to conform to a dorsal side of wearer's wrist joint and the protrusion adapted to extend over a back of a wearer's hand, for preventing hyperextension of the wearer's wrist beyond the fixed angle;
    wherein the fixed angle is configured to promote a dorsal wrist angle suitable for the administration of CPR; and
    wherein the wearable support is adapted to be in close contact with the at least one of the wearer's wrist, hand or forearm, to provide support to the wearer through compression of the at least one of the wearer's wrist, hand or forearm.

2. The device of claim 1 further comprising a fastener for fastening the wearable support in close contact with the at least one of the wearer's wrist, hand or forearm.

3. The device of claim 1 further comprising a support plate on the wearable support, the support plate being substantially rigid and adapted to be in close contact with the at least one of the wearer's wrist, hand or forearm.

4. The device of claim 3 wherein the wearable support has at least one pocket for inserting the support plate and the wearable support is adapted to hold the support plate in close contact with the at least one of the wearer's wrist, hand or forearm.

5. The device of claim 3 wherein there are at least two support plates adapted to conform respectively to a ventral side and a dorsal side of the at least one of the wearer's wrist, hand or forearm.

6. The device of claim 5 wherein one of the at least two support plates is a dorsal plate adapted to conform to the dorsal side of the at least one of the wearer's wrist, hand or forearm, and the hyperextension barrier is integral with the dorsal plate.

7. The device of claim 3 wherein the support plate is adapted to conform to the wearer's wrist, and is adapted to be in close contact with the wearer's wrist.

8. The device of claim 3 wherein the support plate comprises a material selected from the group consisting of: a rigid polymer material, a semi-rigid polymer material, a rigid cardboard material, and combinations thereof.

9. The device of claim 8 wherein the rigid polymer material is polyethylene or polypropylene.

10. The device of claim 3 wherein the hyperextension barrier is integral with the support plate.

11. The device of claim 1 further comprising a palmar pad adapted to conform to a palm side of the wearer's hand, for supporting the wearer's palm.

12. The device of claim 11 wherein the palmar pad is substantially rigid and has a fixed elevation angle corresponding to a heel of the wearer's palm, the palmar pad being adapted to support the heel of the wearer's palm at the fixed elevation angle for maintaining elevation of the wearer's wrist.

13. The device of claim 1 wherein the wearable support has a thumb loop for looping over the wearer's thumb.

14. The device of claim 1 wherein the wearable support is in the form of a glove.

15. The device of claim 14 wherein the glove is a fingerless glove.

16. The device of claim 1 wherein the support device provides support to at least one of the hand, wrist, hand, and forearm of the wearer.

17. The device of claim 1 wherein the wearable support comprises a material selected from the group consisting of an elastic material, a textile material, a polymer material, a flexible material, a semi-rigid material, and combinations thereof.

18. The device of claim 17 wherein the polymer material is neoprene or spandex.

19. The device of claim 17 wherein the textile material is a tightly-wound textile.

20. The device of claim 1 further comprising a feedback component for conveying feedback information to the wearer for assisting the wearer in administration of CPR.

21. The device of claim 20 wherein the feedback component is selected from the group consisting of: a visual display, an audio output device, and a tactile output device.

22. The device of claim 20 wherein the feedback component provides audible cues at a rate corresponding to a desired CPR compression rate.

23. The device of claim 1 further comprising a sensor for monitoring a parameter relevant to administration of CPR.

24. The device of claim 23 wherein the sensor is selected from the group consisting of: a physiological sensor, a pressure sensor, a position sensor, and a movement sensor.

25. The device of claim 23 further comprising a feedback component for relaying the monitored parameter to the wearer.

26. The device of claim 23 wherein the sensor is a depth sensor for monitoring depth of CPR compressions, an angle sensor for monitoring angle of CPR compressions, or a rate sensor for monitoring CPR compression rate.

27. The device of claim 26 wherein the depth sensor is selected from the group consisting of: an optical sensor, an electromagnetic coil, and an accelerometer.

* * * * *